United States Patent
Lindsay

(10) Patent No.: US 11,241,566 B1
(45) Date of Patent: Feb. 8, 2022

(54) CLIP FOR URINARY DRAINAGE SYSTEM

(71) Applicant: Erin Jessica Lindsay, Ann Arbor, MI (US)

(72) Inventor: Erin Jessica Lindsay, Ann Arbor, MI (US)

( * ) Notice: Subject to any disclaimer, the term of this patent is extended or adjusted under 35 U.S.C. 154(b) by 0 days.

(21) Appl. No.: 17/490,395

(22) Filed: Sep. 30, 2021

Related U.S. Application Data

(60) Provisional application No. 63/093,967, filed on Oct. 20, 2020.

(51) Int. Cl.
| | | |
|---|---|---|
| *A61M 39/00* | (2006.01) | |
| *A61M 39/10* | (2006.01) | |
| *A61M 25/00* | (2006.01) | |
| *A61F 5/44* | (2006.01) | |
| *A61M 25/02* | (2006.01) | |
| *F16K 7/06* | (2006.01) | |
| *F16L 15/00* | (2006.01) | |

(52) U.S. Cl.
CPC .... *A61M 39/1011* (2013.01); *A61M 25/0017* (2013.01); *A61F 5/44* (2013.01); *A61M 25/0014* (2013.01); *A61M 39/10* (2013.01); *A61M 39/1055* (2013.01); *A61M 2025/024* (2013.01); *A61M 2039/1027* (2013.01); *A61M 2039/1077* (2013.01); *F16K 7/061* (2013.01); *F16L 15/00* (2013.01)

(58) Field of Classification Search
CPC .............. A61M 39/00; A61M 25/0014; A61M 2025/024; A61M 39/10; A61M 39/1011; A61M 2039/1027; A61M 2039/1077; A61M 39/1055; F16K 7/061; F16L 15/00
See application file for complete search history.

(56) References Cited

U.S. PATENT DOCUMENTS

| | | | | |
|---|---|---|---|---|
| 5,702,369 | A | * 12/1997 | Mercereau | A61M 5/3243 604/110 |
| 6,375,231 | B1 | * 4/2002 | Picha | A61M 39/1011 285/114 |
| 2003/0188403 | A1 | * 10/2003 | Lemke | A61M 16/0683 24/338 |
| 2007/0203463 | A1 | 8/2007 | Salvadori et al. | |
| 2009/0287155 | A1 | * 11/2009 | Silich | A61M 25/02 604/174 |
| 2012/0184944 | A1 | 7/2012 | Tomes et al. | |
| 2016/0129222 | A1 | * 5/2016 | Loesener | A61M 25/0097 604/537 |
| 2016/0166822 | A1 | * 6/2016 | Dodson | A61M 39/10 604/533 |
| 2019/0022368 | A1 | * 1/2019 | Hall | A61M 39/04 |

OTHER PUBLICATIONS

Coloplast, Conveen® Contour Leg Bag, Conveen® Strap, Oct. 16, 2017.

* cited by examiner

*Primary Examiner* — Kai H Weng
(74) *Attorney, Agent, or Firm* — MacMillan, Sobanski & Todd, LLC

(57) ABSTRACT

A clip retains tapered connector members which joining tubing sections of a medical fluid drainage system, such as a urinary collection system. The clip has first and second ends configured to bear against external flanges projecting from the tapered connector members. A central body of the clip applies a controllable compression force to the first and second ends for urging the connector members together. The first and second ends include sub-fingers for snapping onto a respective one of the tapered connector members.

20 Claims, 7 Drawing Sheets

CLIP FOR URINARY DRAINAGE SYSTEM

CROSS REFERENCE TO RELATED APPLICATIONS

This application claims the benefit of U.S. Provisional Application Ser. No. 63/093,967, filed Oct. 20, 2020, which is incorporated herein by reference in its entirety.

STATEMENT REGARDING FEDERALLY SPONSORED RESEARCH

Not Applicable.

BACKGROUND OF THE INVENTION

The present invention relates in general to urinary drainage/collection systems, and, more specifically, to a releasable clip for retaining a mid-tubing connector.

Urinary collection bags and associated tubing may be used for several different kinds of patients. For example, a patient with urinary bladder failure may sometimes have urine drained artificially through tubes directly from the kidneys through access ports in the skin, or the bladder may be drained via a Foley catheter (intermittent or indwelling) or a suprapubic catheter. Sections of tubing connect to urine collection bags which can be strapped or taped to the body (e.g., to the legs underneath the pants). The tubing sections usually have critical connections mid-way to allow separation of the collection bag for emptying or changing to a different sized bag, for example.

The urine gradually collects in the bags and is periodically drained by the patient into the toilet when convenient. These bags may stay connected to the patient all the time, night and day. The tubes exiting the body (usually toward the back) vary substantially in length but can be approximately 12"-15" long. The exit tubes may terminate in a tapered member for forming one half of a sealed connection. There is a corresponding (e.g., complementary) tapered member at an end of a second tube that may also be about 12"-15" long and which is affixed (e.g., permanently attached) distally to the urine collection bag. In some cases, one tapered member is a male connector formed of a firm elastomeric material and the other tapered member is a female connector formed as a more rigid plastic molded part. A matching taper provides end-to-end mating. In order to easily fit beneath the patient's clothing and to facilitate a simple and easy manner of making or breaking the connection while not requiring significant strength or dexterity, a force-fit tapered connection is the most common type of connector used for joining the two sections of tubing.

This mid-way connection has a frequent and unpleasant habit of coming apart since the only thing holding it together is the interference push fit which is completed by the user. Urine acts as a lubricant, and the lubricity eventually loosens the joint, thereby causing it to inadvertently separate and leak.

SUMMARY OF THE INVENTION

The connection halves of the tapered mid-way connector typically have an increased-diameter flange which provides a gripping surface to either push together or pull apart the connector members as required. The invention takes advantage of these flanges to have surfaces to push against using an easily installable/removable clip or clamp. In some embodiments, a clip may be comprised of a one-piece, injection-molded "C" shaped clip (e.g., about 25-30 mm diameter and about 16-18 mm in height). The body of the C-clip may be about 3 mm thick and may follow a shape of an oval, circle, or other contour having curved or straight segments. The C-clip may preferably comprise a plastic, multi-acting spring. At the top and bottom of the C ends there are two opposing spring "fingers." The main "fingers" curve inward towards each other and each one has a pair of sub-fingers that partially wrap around the respective plastic tubing connector members. The sub-fingers at each end of the C also are springs that allow flexing apart and snapping the device on and off repeatedly every day. Thus, this clip has a total of three spring sections: 1) a main (e.g., "C-shaped") spring forcing the two halves of the tube connection together, 2) sub-fingers (e.g., having a C-shaped inner edge) at one end of the large C spring to elastically grasp one side of the connector (e.g., one tapered member at its flange), and 3) C-shaped sub-fingers at the other end of the large C spring to elastically grasp the other side of the connector (e.g., the other tapered member at its flange). Also, the terminal ends of the large C spring adjacent the sub-fingers simultaneously has a reverse curving section (i.e., an outward curve). The apex where the direction of the curve reverses becomes the narrowest section (i.e., neck) of the C spring. The center of the recess between sub-fingers coincides with the narrow neck portion so that the action points between the ends of the clip and the flanges on the tapered members are located on a plane that bisects the connector along its central longitudinal axis. This helps ensure that the spring action compressing the connector concentrates the compression force along a coaxial direction of the tubing flanges.

The C-clip can be comprised of Delrin (acetal) plastic because it has long-term memory and makes good springs. Other materials, including thin metal or other plastics, could also be used. An appropriate amount of spring force at each of the three spring sections may be obtained when using various different materials by adjusting the thickness profiles at respective portions of the clip accordingly.

DETAILED DESCRIPTION OF PREFERRED EMBODIMENTS

Figure 1:
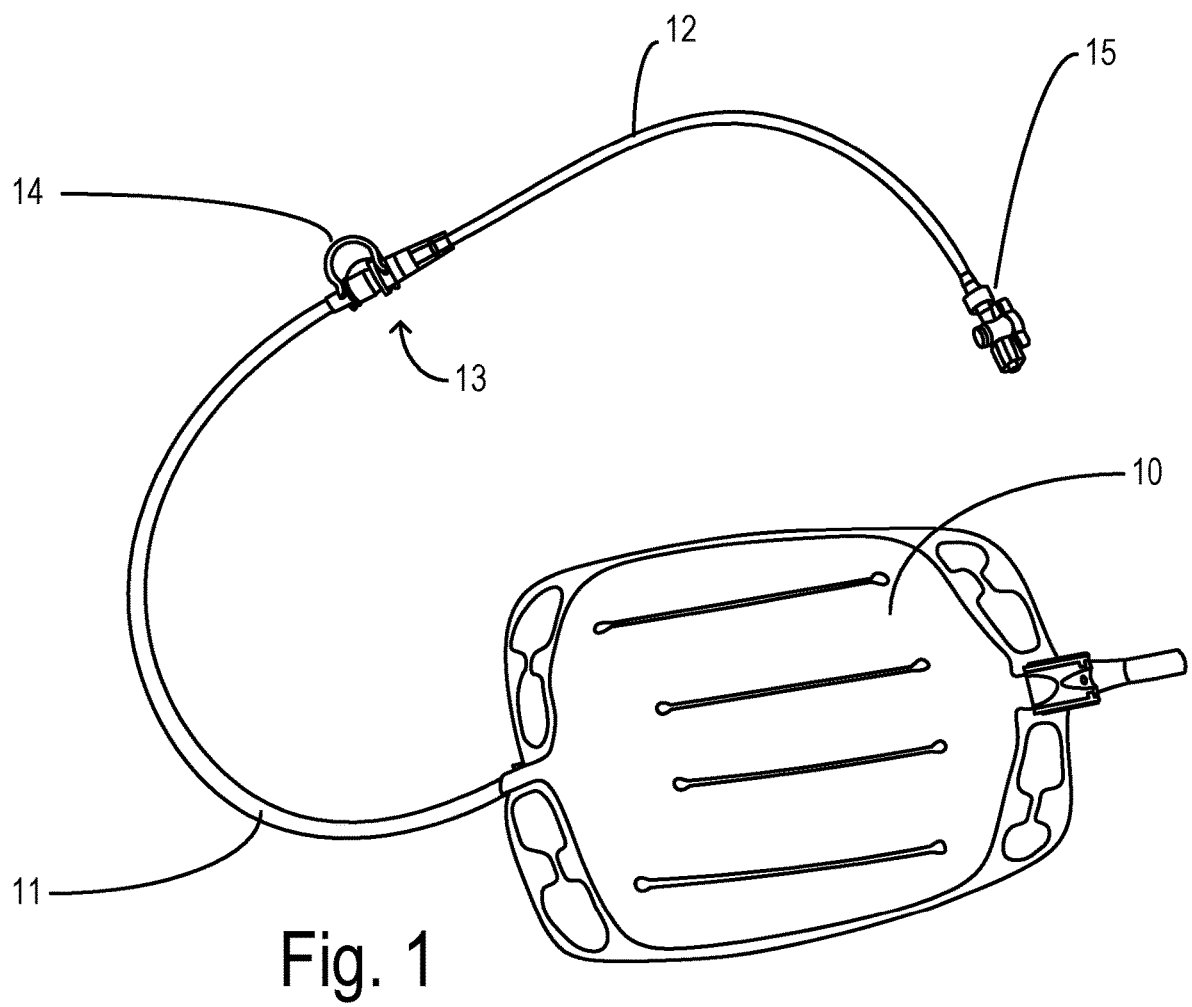
FIG. 1 is a schematic view of a urinary collection system.
Figure 2:
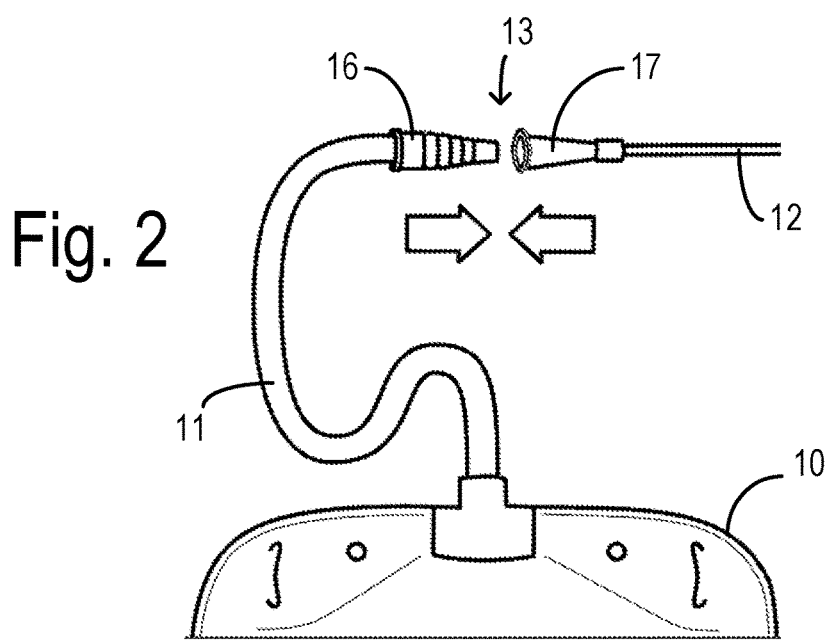
FIG. 2 is a schematic view showing the making of a mid-way connection.

As shown in FIG. 1, a urinary collection bag 10 has an integral first tubing section 11 connected to a second tubing section 12 by a tapered mid-way connector 13. Midway tubing connector 13 is robustly held together in the present invention by a clip 14 which can be manually installed and removed with minimal effort. A second end of tubing section 12 may be fitted to a control valve 15 which further connects to the patient's catheter or catheter tubing. FIG. 2 illustrates how the tapered connectors are manually joined and separated in order to make collection bag 10 removable/replaceable.

Figure 3:
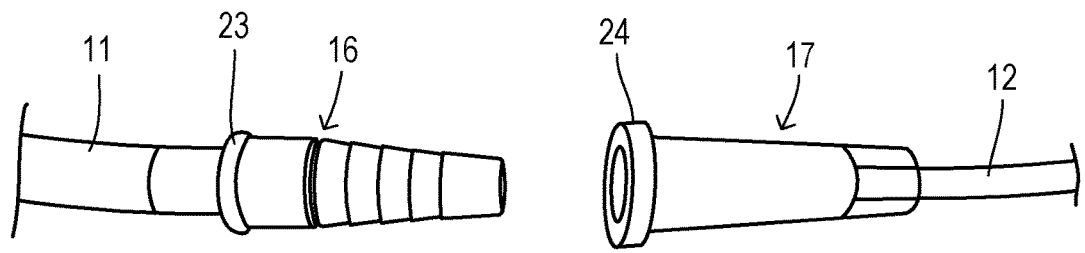
FIG. 3 is a schematic view showing a mid-way connection in greater detail.
Figure 4:
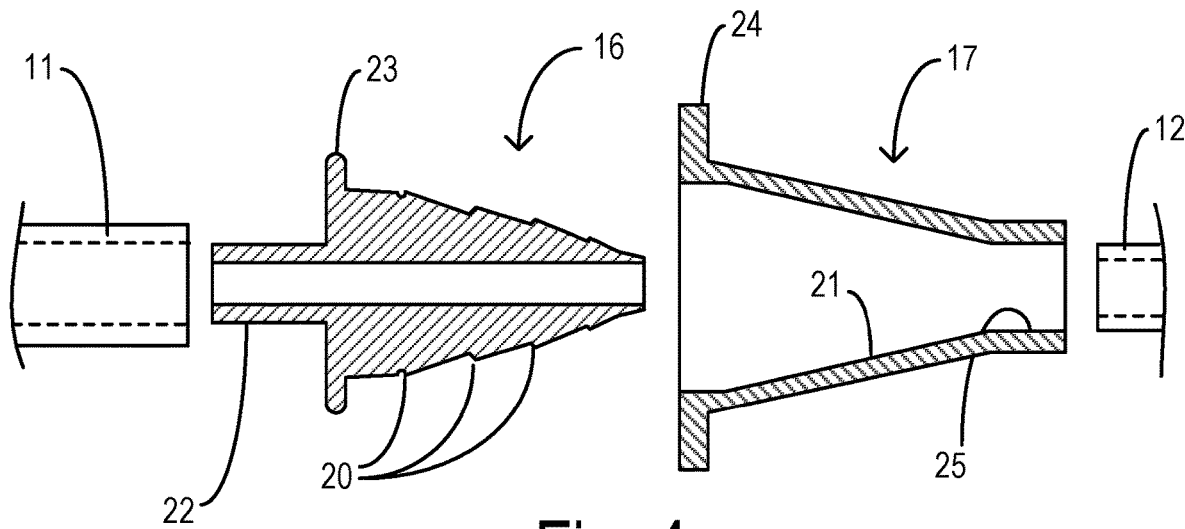
FIG. 4 is a cross-sectional view of mid-way connectors.
Figure 5:
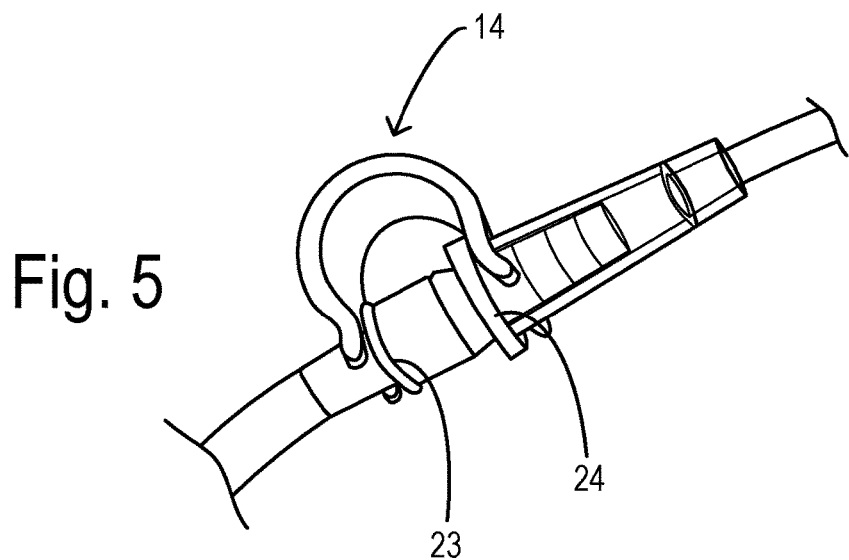
FIG. 5 is a perspective view showing a retention clip of the invention securing the mid-way connectors of FIG. 3.
Figure 6:
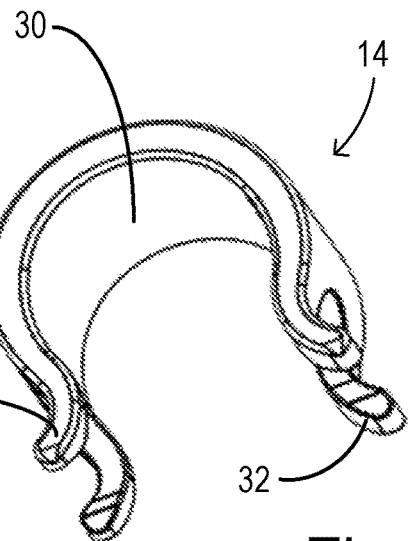
FIG. 6 is an end perspective view of the clip of FIG. 3.

Connector 13 is shown in greater detail in FIGS. 3-5 wherein tubing section 11 terminates with a tapered male connector member 16. Tubing section 12 terminates with a female tapered connector member 17. Connector member 16 includes a series of concentric barbs 20 which engage an internal tapered section 21 of connector member 17 to create a seal. Male connector member 16 has a stem 22 which is retained inside the interior of tubing 11. Male connector member 16 has a gripping flange 23 which approaches a gripping flange 24 on female connector member 17 during interconnection. Female connector member 17 has an open end passage 25 for securely receiving tubing section 12 to provide a seal. Female connector member 17 may be formed of a clear, stiff plastic. Male connector member 16 may be formed of a slightly resilient elastomeric material which is slightly compressible when the matching tapers are engaged in order to achieve a press fit.

Clip 14 is shown in greater detail in FIGS. 6-12. Clip 14 has a center body portion 30 (e.g., having a C shape) and has ends 31 and 32 which transition from the inward C-shaped curvature to a reverse (outward) curvature. In some embodiments, clip 14 is a C-shaped band formed by a continuous sheet. Each end 31 and 32 has its own C-shape opening with a pair of sub-fingers for grasping respective sides of connector 13, wherein the C-shape defined along inner edges of the sub-fingers is oriented transversely to the main C-shape. Because of the different characteristics of the two connector halves, the diameters of the openings in ends 31 and 32 between the sub-fingers are also different. Furthermore, end 31 which grasps male connector member 16 over a portion of the flexible (e.g., compressible) tubing section 11 has a smaller diameter than end 32 which captures a rigid (and larger) diameter portion of female connector 17.

Figure 7:
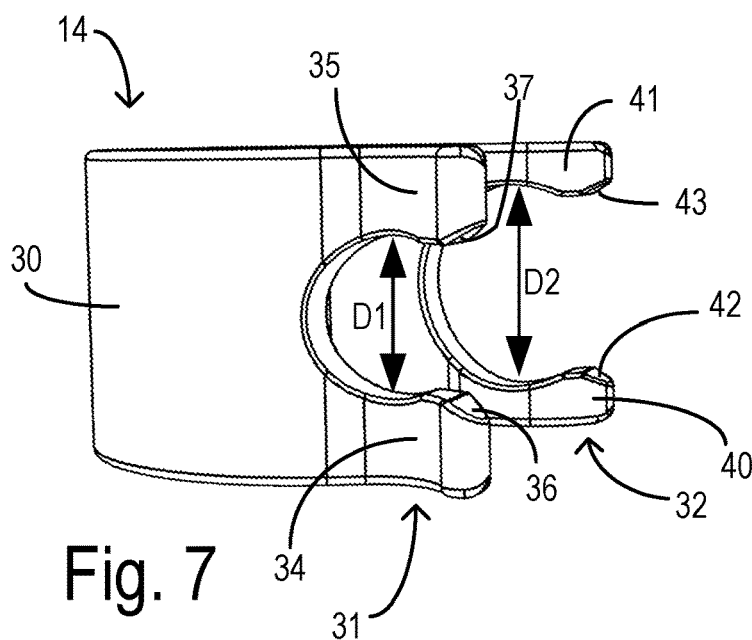
FIG. 7 is a side view of the clip of FIG. 3 depicting diameters of the central openings.
Figure 8:
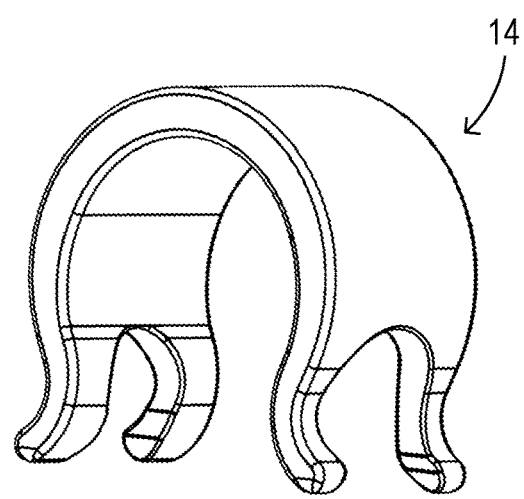
FIG. 8 is another perspective view of the clip of FIG. 3.
Figure 9:
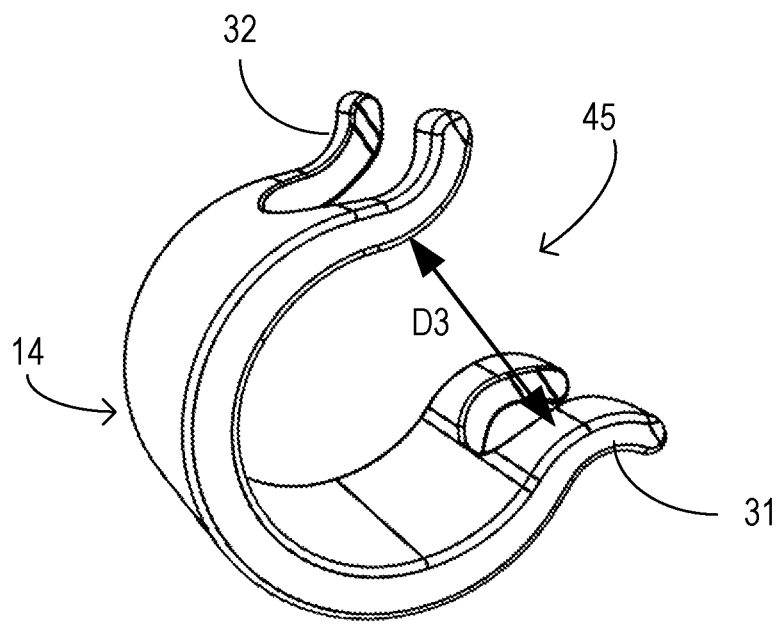
FIG. 9 is an end perspective view of the clip of FIG. 3 showing the main opening and transition to a reverse curvature.

As seen in FIG. 7, end 31 includes sub fingers 34 and 35 defining a central opening having a diameter D1. Open ends of the C-shaped sub-fingers include sloped edges 36 and 37 to facilitate insertion over the connector/tubing portion of male connector member 16. Similarly, end 32 has a pair of sub-fingers 40 and 41 defining a central opening having a diameter D2 which is larger than D1 in order to accommodate the configuration of female connector member 17. Sloped edges 42 and 43 facilitate insertion of end 32 over female connector member 17. Each sub-finger 34, 35, 40, and 41 is slightly deformable to achieve a snap fit onto the respective portions of the connector. As shown in FIG. 9, a main opening 45 (i.e., a neck portion) of C-clip 14 has a minimum separation distance D3 between ends 31 and 32. The band defining main opening 45 also defines a radius which results in a reverse curvature section so that the neck portion (e.g., between central body portion 30 and each of ends 31 and 32) defines a sloped opening for guiding C-clip 14 onto the mid-way connector. When installed on the connector, the points corresponding to closest approach at D3 are aligned on diametrically opposite sides of the flanges so that a compression force holding the connector members together is parallel with a center axis of connector 13 and the tubing sections. If desired, the sub-fingers may have corresponding flats to facilitate a smooth insertion and removal of the connector members (e.g., flats 60 and 61 in FIG. 12). band defines reverse curvature sections which engages the external flanges at radially opposing locations.

Figure 10:
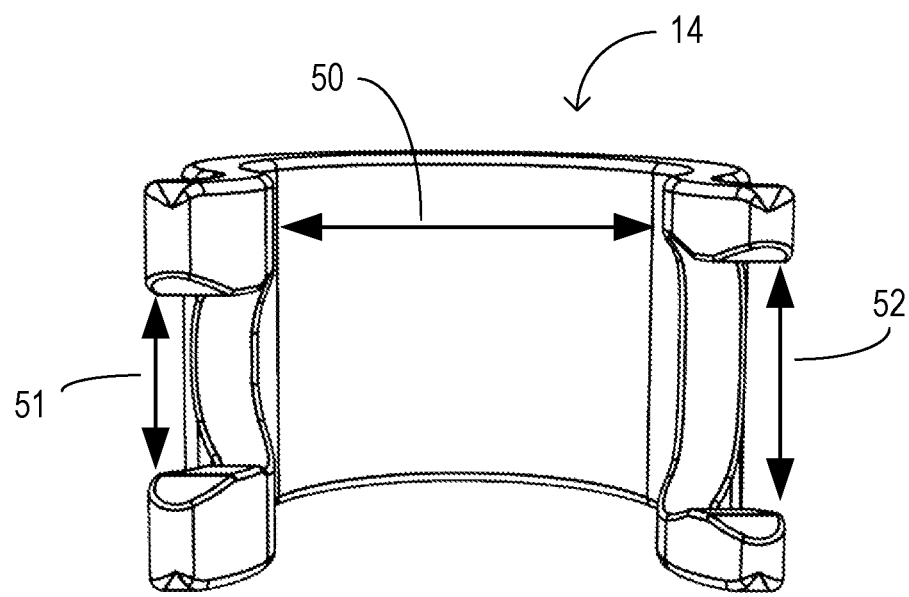
FIG. 10 is a side view of the clip of FIG. 3.
Figure 11:
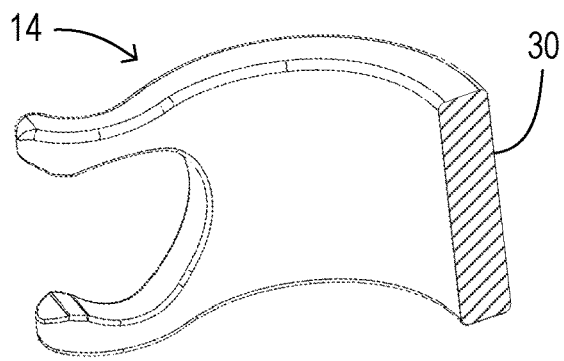
FIG. 11 is a cross-sectional, perspective view of the clip of FIG. 3.
Figure 12:
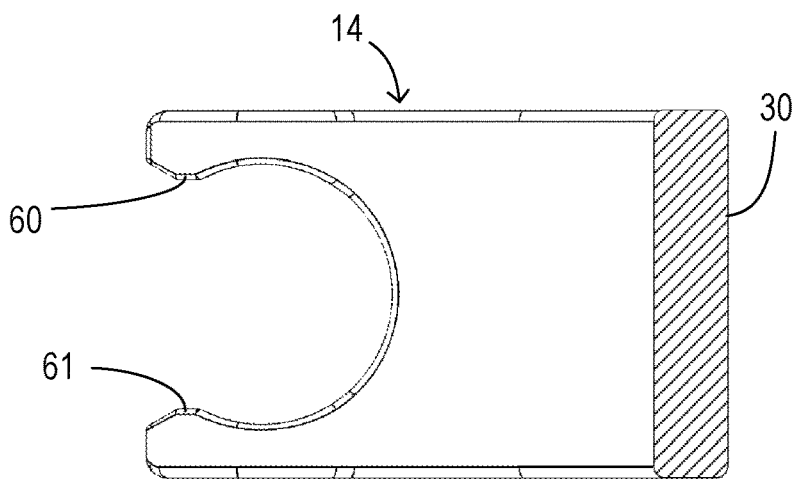
FIG. 12 is a side cross-sectional view of the clip of FIG. 3.

FIG. 10 shows the directions of the multi-acting springs inherent in clip 14. A spring action 50 provides a clamping force to keep the tapered connector members together along a center axial direction (liquid flow direction) of the connection. Spring actions 51 and 52 provide clamping forces to laterally retain clip 14 on the connector members.

Figure 13:
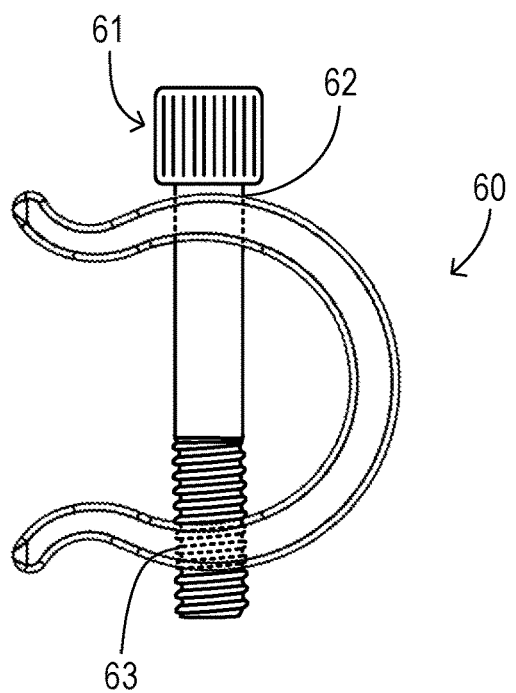
FIG. 13 is an end view of the clip of FIG. 3.

FIG. 13 shows an alternative embodiment of a C-clip 60 wherein a threaded screw or pin 61 is provided through the main body portion of the C-clip in order to rigidify the corresponding spring action after installation of the clip onto a connector in order to further ensure against accidental removal of the clip. Screw 61 passes freely through a first aperture 62 on one side of C-clip 60 and has a threaded end which turns within a threaded aperture 63 on the other side of C-clip 60. For installation/removal of clip 60, screw 61 is retracted to allow clip 60 to expand. For retention, screw 61 is advanced so that an enlarged head of screw 61 bears against clip 60 and prevents it from flexing open. Since threaded screw 61 passes through diametrically opposed apertures 62/63 in central body 30, and since the enlarged head portion is juxtaposed with aperture 62 on an external surface of central body 30, turning of threaded screw 61 applies a controllable compression between the neck portion at the first and second ends of clip 60.

Figure 14:
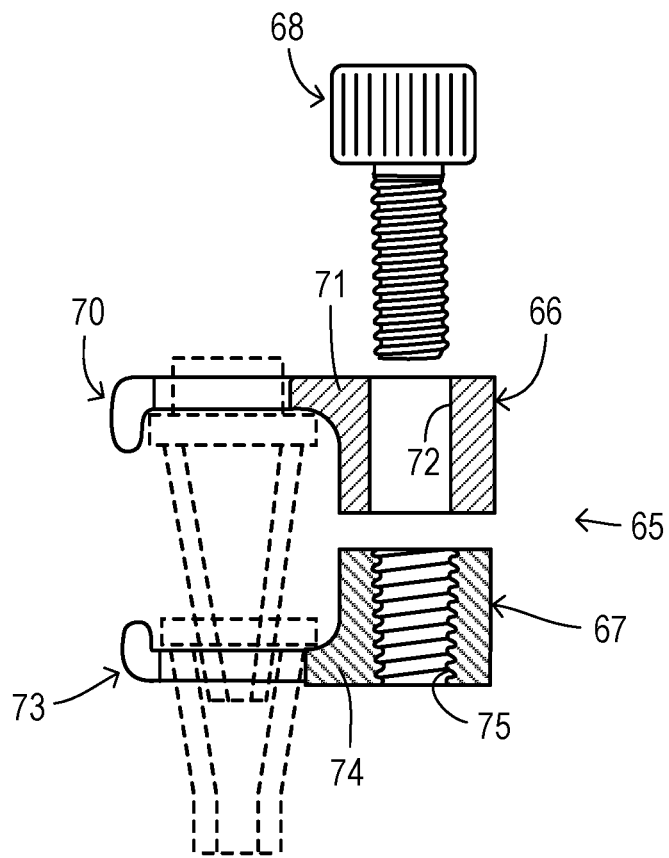
FIG. 14 is a side cross-sectional view of an alternative embodiment of a retention clip.

FIG. 14 shows an alternative embodiment wherein a clip 65 comprises an upper member 66 and a lower member 67 joined by a threaded screw or pin 68. Upper member 66 has a connector end 70 which comprises a pair of C-shaped sub-fingers (not shown) for snapping onto and grasping a male portion of the mid-way connector in the same way as in the prior embodiments. Member 66 has a base portion 71 with an aperture 72 freely accommodating a shaft of screw 68. Lower member 67 has a connector end 73 which comprises a pair of C-shaped sub-fingers for snapping onto and grasping a female portion of the mid-way connector in the same way as in the prior embodiments. Member 67 has a base portion 74 with a threaded aperture 75 into which the shaft of screw 68 is rotatable.

Figure 15:
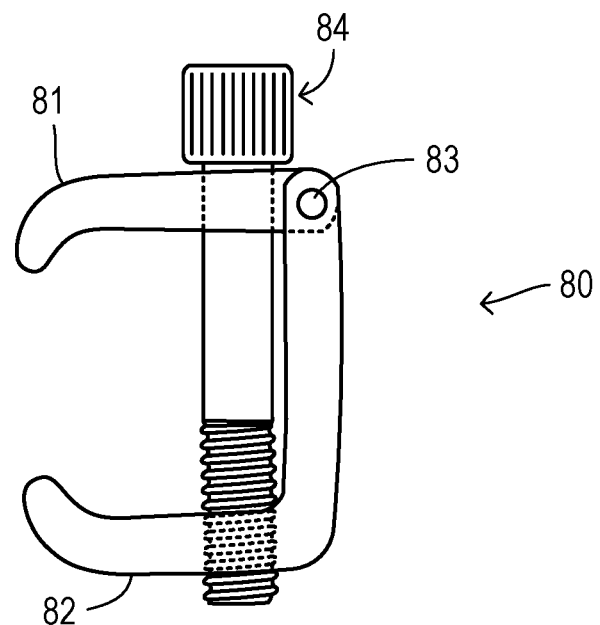
FIG. 15 is a side view of another alternative embodiment of a retention clip.

In FIG. 14, upper and lower member 66/67 are separable. FIG. 15 shows an alternative embodiment of a clip 80 wherein an upper member 81 and a lower member 82 are pivotably connected by a hinge pin 83. Members 81 and 82 likewise include respective pairs of C-shaped sub-fingers and respective unthreaded and threaded apertures for receiving a threaded screw or pin 84. The unthreaded aperture in upper member 81 may provide sufficient space to accommodate a slight change in angle at which screw 84 passes through when members 81/82 pivot about hinge pin 83.

Figure 16:
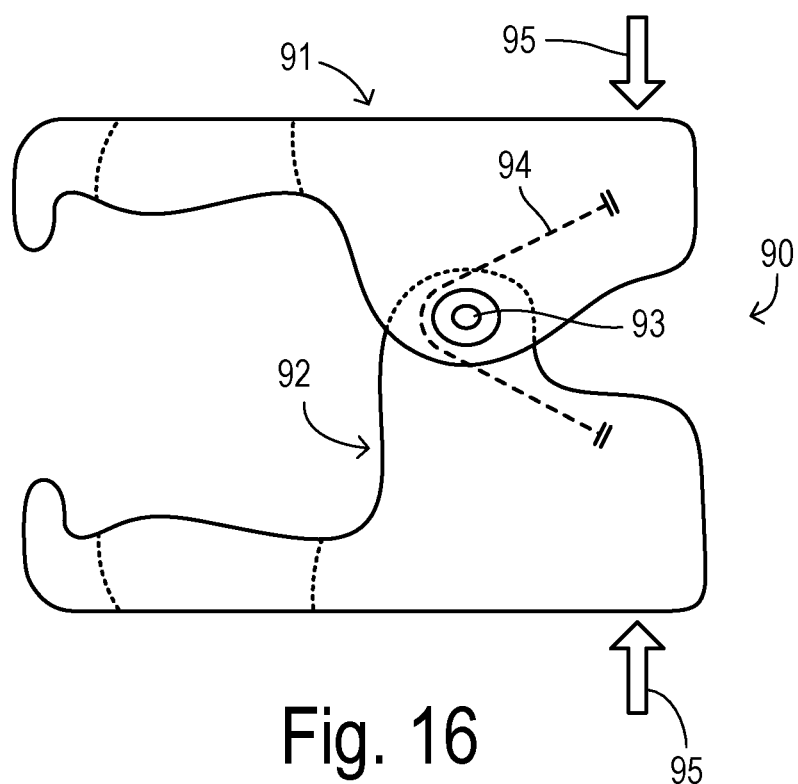
FIG. 16 is a side cross-sectional view of another alternative embodiment of a retention clip.
Figure 17:
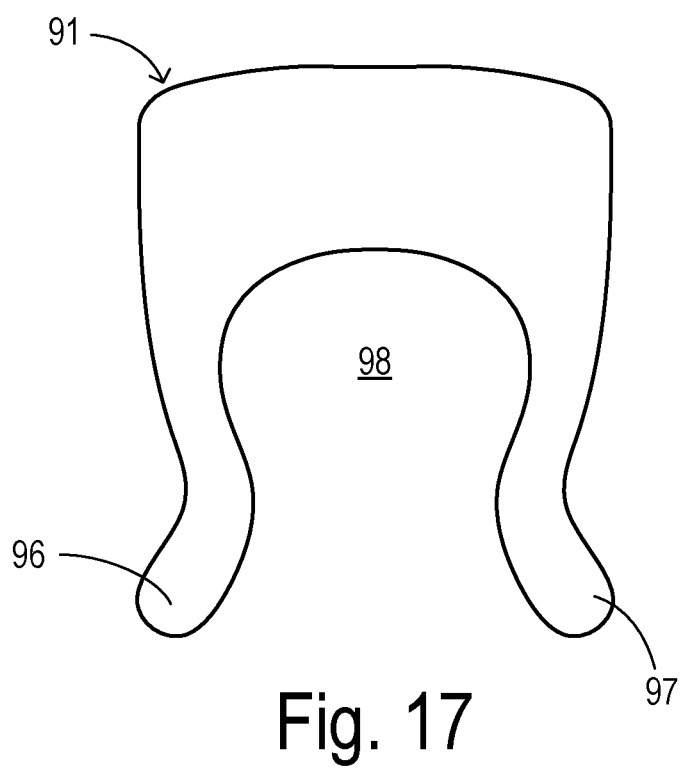
FIG. 17 is a top view of the clip of FIG. 16.

FIG. 16 shows an alternative embodiment of a C-clip 90 using a spring-loaded scissor joint. An upper member 91 is pivotably joined to a lower member 92 by a hinge pin 93. Members 91/92 likewise include respective pairs of C-shaped sub-fingers at one end for snapping onto the male and female connectors of the mid-way connection. A bias spring 94 has opposite ends affixed to members 91 and 92, respectively, so that the ends of members 91/92 having the sub-fingers are urged together in a manner that clamps the mid-way connection. To overcome the spring force when installing or removing clip 90, a user presses on the opposite ends of members 91 and 92 as shown by arrows 95. The top view of FIG. 16 shows a respective set of sub-fingers 96 and 97 of upper member 91 along with a central opening 98 which receives one of the connectors of the mid-way connection.

What is claimed is:

1. A clip for retaining tapered connector members joining tubing sections of a medical fluid drainage system, comprising:
   first and second ends configured to bear against external flanges projecting from the tapered connector members; and
   a central body applying a controllable compression force to the first and second ends for urging the tapered connector members toward one another to join the tapered connector members;
   wherein the first and second ends include sub-fingers for snapping onto a respective one of the tapered connector members with the external flanges arranged between the first and second ends.

2. The clip of claim 1 wherein the central body and first and second ends are comprised of a C-shaped band formed by a continuous sheet.

3. The clip of claim 2 wherein the band defines reverse curvature sections between the central body and each of the first and second ends to provide a neck which engages the external flanges at radially opposing locations.

4. The clip of claim 2 wherein each of the first and second ends includes a respective pair of sub-fingers defining a respective C-shaped opening having a respective diameter configured to retain a respective one of the tapered connector members.

5. The clip of claim 2 further comprising a threaded member passing through diametrically opposed apertures in the central body, wherein a first one of the apertures has a threaded internal surface receiving the threaded member, and wherein the threaded member has a head portion juxtaposed with a second one of the apertures, so that turning of the threaded member applies a controllable compression between the first and second ends.

6. The clip of claim 2 wherein the C-shaped band is comprised of a molded plastic material.

7. The clip of claim 1 wherein the sub-fingers include respective sloped edges configured to receive a respective tapered connector member during insertion of the respective tapered connector member into a respective C-shaped opening between the sub-fingers.

8. The clip of claim 1 wherein the central body is comprised of first and second base portions of an upper clip member and a lower clip member, respectively, and wherein the first and second ends are formed on the upper and lower clip members opposite the first and second base portions, respectively.

9. The clip of claim 8 wherein the upper and lower clip members are coupled by a threaded member to compress the first and second ends against the external flanges.

10. The clip of claim 8 further comprising:
    a hinge pin for coupling the upper clip member to the lower clip member to provide a scissor-like movement; and
    a bias spring coupled between the upper and lower clip members to compress the first and second ends against the external flanges.

11. A clip for retaining tapered connector members of a mid-way connector which joins urinary tubing sections of a urinary bag collection system, comprising:
    first and second ends configured to bear against external flanges projecting from the tapered connector members; and
    a central body applying a controllable compression force to the first and second ends for urging the tapered connector members toward one another to join the tapered connector members;
    wherein the first and second ends include sub-fingers for snapping onto a respective one of the tapered connector members with the external flanges arranged between the first and second ends.

12. The clip of claim 11 wherein the central body and first and second ends are comprised of a C-shaped band formed by a continuous sheet.

13. The clip of claim 12 wherein the band defines reverse curvature sections between the central body and each of the first and second ends to provide a neck which engages the external flanges at radially opposing locations.

14. The clip of claim 12 wherein each of the first and second ends includes a respective pair of sub-fingers defining a respective C-shaped opening having a respective diameter configured to retain a respective one of the tapered connector members.

15. The clip of claim 12 further comprising a threaded member passing through diametrically opposed apertures in the central body, wherein a first one of the apertures has a threaded internal surface receiving the threaded member, and wherein the threaded member has a head portion juxtaposed with a second one of the apertures, so that turning of the threaded member applies a controllable compression between the first and second ends.

16. The clip of claim 12 wherein the C-shaped band is comprised of a molded plastic material.

17. The clip of claim 11 wherein the sub-fingers include respective sloped edges configured to receive a respective tapered connector member during insertion of the respective tapered connector member into a respective C-shaped opening between the sub-fingers.

18. The clip of claim 11 wherein the central body is comprised of first and second base portions of an upper clip member and a lower clip member, respectively, and wherein the first and second ends are formed on the upper and lower clip members opposite the first and second base portions, respectively.

19. The clip of claim 18 wherein the upper and lower clip members are coupled by a threaded member to compress the first and second ends against the external flanges.

20. The clip of claim 18 further comprising:
    a hinge pin for coupling the upper clip member to the lower clip member to provide a scissor-like movement; and
    a bias spring coupled between the upper and lower clip members to compress the first and second ends against the external flanges.

* * * * *